(12) United States Patent
Fukuoka et al.

(10) Patent No.: US 8,044,167 B2
(45) Date of Patent: *Oct. 25, 2011

(54) PROCESS FOR PRODUCTION OF HIGH-PURITY DIARYL CARBONATE

(75) Inventors: Shinsuke Fukuoka, Tokyo (JP); Hironori Miyaji, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 121 days.

This patent is subject to a terminal disclaimer.

(21) Appl. No.: 12/508,331

(22) Filed: Jul. 23, 2009

(65) Prior Publication Data

US 2009/0287014 A1 Nov. 19, 2009

Related U.S. Application Data

(62) Division of application No. 11/660,902, filed as application No. PCT/JP2005/018768 on Oct. 12, 2005, now Pat. No. 7,622,601.

(30) Foreign Application Priority Data

Oct. 14, 2004 (JP) ................................. 2004-299793

(51) Int. Cl.
*C07G 64/00* (2006.01)
(52) U.S. Cl. ........................................ 528/198; 560/106
(58) Field of Classification Search .................. 560/106; 528/198

See application file for complete search history.

(56) References Cited

U.S. PATENT DOCUMENTS

| | | |
|---|---|---|
| 3,888,826 A | 6/1975 | Yamana et al. |
| 4,045,464 A | 8/1977 | Romano et al. |
| 4,182,726 A | 1/1980 | Illuminati et al. |
| 4,252,737 A | 2/1981 | Krimm et al. |
| 4,410,464 A | 10/1983 | Hallgren |
| 4,552,704 A | 11/1985 | Mark |
| 4,554,110 A | 11/1985 | Mark |
| 4,609,501 A | 9/1986 | Mark |
| 5,210,268 A | 5/1993 | Fukuoka et al. |
| 5,231,212 A | 7/1993 | Buysch et al. |
| 5,282,965 A | 2/1994 | Urairi et al. |
| 5,284,965 A | 2/1994 | Buysch et al. |
| 5,334,742 A | 8/1994 | Schon et al. |
| 5,344,954 A | 9/1994 | Schon et al. |
| 5,359,118 A | 10/1994 | Wagner et al. |
| 5,362,901 A | 11/1994 | Wagner et al. |
| 5,426,207 A | 6/1995 | Harrison et al. |
| 5,495,038 A | 2/1996 | Buysch et al. |
| 5,705,673 A | 1/1998 | Rivetti et al. |
| 5,747,609 A | 5/1998 | Komiya et al. |
| 5,840,826 A | 11/1998 | Komiya et al. |
| 5,872,275 A | 2/1999 | Komiya et al. |
| 6,093,842 A | 7/2000 | Oyevaar et al. |
| 6,197,916 B1 | 3/2001 | Pressman et al. |
| 6,262,210 B1 | 7/2001 | Tojo et al. |
| 6,265,526 B1 | 7/2001 | Komiya et al. |
| 6,320,015 B1 | 11/2001 | Komiya et al. |
| 6,346,638 B1 | 2/2002 | Tojo et al. |
| 6,429,276 B1 | 8/2002 | Komiya et al. |
| 6,479,689 B1 | 11/2002 | Tojo et al. |
| 6,861,494 B2 | 3/2005 | Debruin |
| 6,953,864 B2 | 10/2005 | De Jonge et al. |
| 7,417,161 B2 | 8/2008 | Woo et al. |
| 7,479,258 B2 * | 1/2009 | Fukuoka et al. ............... 422/131 |
| 7,531,616 B2 | 5/2009 | Fukuoka et al. |
| 7,622,601 B2 | 11/2009 | Fukuoka et al. |
| 2001/0021786 A1 | 9/2001 | Bruin et al. |
| 2002/0107355 A1 | 8/2002 | Bouwens et al. |
| 2004/0236136 A1 | 11/2004 | Schlosberg et al. |
| 2004/0266974 A1 | 12/2004 | Murthy et al. |
| 2007/0148055 A1 | 6/2007 | Fukuoka et al. |
| 2007/0191623 A1 | 8/2007 | Fukuoka et al. |
| 2007/0219387 A1 | 9/2007 | Fukuoka et al. |
| 2007/0255069 A1 | 11/2007 | Fukuoka et al. |
| 2007/0260083 A1 | 11/2007 | Fukuoka et al. |
| 2007/0260084 A1 | 11/2007 | Fukuoka et al. |
| 2007/0260095 A1 | 11/2007 | Fukuoka et al. |

(Continued)

FOREIGN PATENT DOCUMENTS

DE 736063 6/1943

(Continued)

OTHER PUBLICATIONS

US Office Action for co-pending U.S. Appl. No. 11/660,362 issued Dec. 17, 2009.

*Primary Examiner* — Rei-tsang Shiao

(74) *Attorney, Agent, or Firm* — Birch, Stewart, Kolasch & Birch, LLP

(57) ABSTRACT

An aromatic polycarbonate that is obtained by transesterification between a high-purity diphenyl carbonate and an aromatic dihydroxy compound. A specific industrially useful process for the production of a high-purity diaryl carbonate in which a diaryl carbonate having low contents of intermediate boiling point and high boiling point impurities is produced is disclosed. As a starting material, a reaction mixture containing an alkyl aryl carbonate obtained through a transesterification reaction between a dialkyl carbonate and an aromatic monohydroxy compound is used. The process in which separation by distillation is carried out uses three distillation columns in a specified order. Moreover, it is particularly preferable if a reactive distillation column and the three distillation columns, each of which has a specified structure, and the three distillation columns are each operated under specified distillation conditions.

4 Claims, 1 Drawing Sheet

U.S. PATENT DOCUMENTS

| | | |
|---|---|---|
| 2007/0265461 A1 | 11/2007 | Fukuoka et al. |
| 2007/0270604 A1 | 11/2007 | Fukuoka et al. |
| 2008/0041712 A1 | 2/2008 | Fukuoka et al. |
| 2008/0051595 A1 | 2/2008 | Fukuoka et al. |
| 2008/0064846 A1 | 3/2008 | Fukuoka et al. |
| 2008/0221348 A1 | 9/2008 | Fukuoka et al. |
| 2009/0118530 A1 | 5/2009 | Fukuoka et al. |
| 2009/0163734 A1 | 6/2009 | Fukuoka et al. |

FOREIGN PATENT DOCUMENTS

| | | |
|---|---|---|
| EA | 009715 B1 | 2/2008 |
| EA | 010066 B1 | 6/2008 |
| EP | 0 461 274 A1 | 12/1991 |
| EP | 0530615 A2 | 3/1993 |
| EP | 0560159 A1 | 9/1993 |
| EP | 0569812 A1 | 11/1993 |
| EP | 0582930 A2 | 2/1994 |
| EP | 0582931 A2 | 2/1994 |
| EP | 0722931 A1 | 7/1996 |
| EP | 0784048 A1 | 1/1997 |
| EP | 0 784 048 A1 | 7/1997 |
| EP | 0781760 A1 | 7/1997 |
| EP | 0855384 A1 | 7/1998 |
| EP | 0892001 A1 | 1/1999 |
| EP | 1016648 A1 | 7/2000 |
| EP | 1 048 685 A1 | 11/2000 |
| EP | 1086940 A1 | 3/2001 |
| EP | 1174406 A1 | 1/2002 |
| EP | 1 760 069 A1 | 3/2007 |
| EP | 1762560 A1 | 3/2007 |
| EP | 1762599 A1 | 3/2007 |
| EP | 1767517 A1 | 3/2007 |
| EP | 1767518 | 3/2007 |
| EP | 1 783 112 A1 | 5/2007 |
| EP | 1 787 977 A1 | 5/2007 |
| EP | 1792890 A1 | 6/2007 |
| EP | 1795523 A1 | 6/2007 |
| GB | 1007302 | 10/1965 |
| IT | 1255746 B | 11/1995 |
| JP | 51-75044 B | 6/1976 |
| JP | 51-105032 A | 9/1976 |
| JP | 52-36159 | 9/1977 |
| JP | 54-48732 A | 4/1979 |
| JP | 54-48733 A | 4/1979 |
| JP | 54-63023 A | 5/1979 |
| JP | 56-25138 A | 3/1981 |
| JP | 56-123948 A | 9/1981 |
| JP | 56-123949 A | 9/1981 |
| JP | 57-176932 A | 10/1982 |
| JP | 57-183745 A | 11/1982 |
| JP | 58-185536 A | 10/1983 |
| JP | 60-169444 A | 9/1985 |
| JP | 60-169445 A | 9/1985 |
| JP | 60-173016 A | 9/1985 |
| JP | 61-172852 A | 8/1986 |
| JP | 61-291545 A | 12/1986 |
| JP | 62-277345 A | 12/1987 |
| JP | 1-93560 A | 4/1989 |
| JP | 1-265062 A | 10/1989 |
| JP | 1-265063 A | 10/1989 |
| JP | 1-265064 A | 10/1989 |
| JP | 2-153923 A | 6/1990 |
| JP | 3-291257 A | 12/1991 |
| JP | 4-9358 A | 1/1992 |
| JP | 4-100824 A | 4/1992 |
| JP | 4-198141 A | 7/1992 |
| JP | 4-211038 A | 8/1992 |
| JP | 4-224547 A | 8/1992 |
| JP | 4-230242 A | 8/1992 |
| JP | 4-235951 A | 8/1992 |
| JP | 5-213830 A | 8/1993 |
| JP | 6-9506 A | 1/1994 |
| JP | 6-9507 A | 1/1994 |
| JP | 6-41022 A | 2/1994 |
| JP | 6-157424 A | 6/1994 |
| JP | 6-184058 A | 7/1994 |
| JP | 7-101908 A | 4/1995 |
| JP | 7-304713 A | 11/1995 |
| JP | 8-225641 A | 9/1996 |
| JP | 8-225643 A | 9/1996 |
| JP | 8-325373 A | 12/1996 |
| JP | 9-40616 A | 2/1997 |
| JP | 9-59224 A | 3/1997 |
| JP | 9-59225 A | 3/1997 |
| JP | 9-110805 A | 4/1997 |
| JP | 9-165357 A | 6/1997 |
| JP | 9-169704 A | 6/1997 |
| JP | 9-173819 A | 7/1997 |
| JP | 9-176094 A | 7/1997 |
| JP | 9-194435 A | 7/1997 |
| JP | 9-194436 A | 7/1997 |
| JP | 9-194437 A | 7/1997 |
| JP | 9-255772 A | 9/1997 |
| JP | 10-81741 A | 3/1998 |
| JP | 10-245366 A | 9/1998 |
| JP | 10-298279 A | 11/1998 |
| JP | 11-12230 A | 1/1999 |
| JP | 11-49727 A | 2/1999 |
| JP | 11-92429 A | 4/1999 |
| JP | 11-140029 A | 5/1999 |
| JP | 11-228504 A | 8/1999 |
| JP | 2000-191596 A | 7/2000 |
| JP | 2000-191597 A | 7/2000 |
| JP | 2001-64234 A | 3/2001 |
| JP | 2001-64235 A | 3/2001 |
| JP | 2002-249575 A | 9/2002 |
| JP | 2003-113144 A | 4/2003 |
| JP | 2003-119168 A | 4/2003 |
| JP | 2003-155264 A | 5/2003 |
| JP | 2003-516376 A | 5/2003 |
| JP | 2003-300936 A | 10/2003 |
| JP | 2003-342209 A | 12/2003 |
| JP | 2004-131421 A | 4/2004 |
| JP | 2004-211107 A | 7/2004 |
| JP | 2004-323384 A | 11/2004 |
| JP | 2006-182683 A | 7/2006 |
| JP | 2006-199643 A | 8/2006 |
| JP | 2006-206497 A | 8/2006 |
| RU | 2 041 869 C1 | 8/1995 |
| WO | WO-91/09832 A1 | 7/1991 |
| WO | WO-92/18458 A1 | 10/1992 |
| WO | WO-97/11049 A1 | 3/1997 |
| WO | WO 97/22650 A1 | 6/1997 |
| WO | WO 99/36457 A1 | 7/1999 |
| WO | WO-99/64382 A1 | 12/1999 |
| WO | WO-99/64492 A1 | 12/1999 |
| WO | WO 99/65970 A1 | 12/1999 |
| WO | WO-00/18720 A1 | 4/2000 |
| WO | WO-00/51954 A1 | 9/2000 |
| WO | WO-01/42187 A1 | 6/2001 |
| WO | WO-02/40439 A2 | 5/2002 |
| WO | WO-03/016257 A1 | 2/2003 |
| WO | WO-03/066569 A1 | 8/2003 |
| WO | WO-2005/123638 A1 | 12/2005 |
| WO | WO-2006-001256 A1 | 1/2006 |
| WO | WO-2006/022294 A1 | 3/2006 |
| WO | WO-2006/025424 A1 | 3/2006 |
| WO | WO-2006/025478 A1 | 3/2006 |
| WO | WO-2006/041075 A1 | 4/2006 |

* cited by examiner

PROCESS FOR PRODUCTION OF HIGH-PURITY DIARYL CARBONATE

This application is a Divisional of application Ser. No. 11/660,902 filed on Feb. 23, 2007 now U.S. Pat. No. 7,622,601 and for which priority is claimed under 35 U.S.C. §120. application Ser. No. 11/660,902 is the national phase of PCT International Application No. PCT/JP2005/018768 filed on Oct. 12, 2005 under 35 U.S.C. §371. The entire contents of each of the above-identified applications are hereby incorporated by reference.

TECHNICAL FIELD

The present invention relates to an industrial process for the production of a high-purity diaryl carbonate. More particularly, the present invention relates to a process for the production of a high-purity diaryl carbonate, which is useful as a raw material of a transesterification method polycarbonate, by taking a reaction mixture containing an alkyl aryl carbonate that has been obtained through a transesterification reaction between a dialkyl carbonate and an aromatic monohydroxy compound as a starting material, and carrying out a transesterification reaction using a reactive distillation column, and then subjecting a reaction mixture containing a diaryl carbonate thus obtained to separation and purification using three continuous multi-stage distillation columns.

BACKGROUND ART

A high-purity diphenyl carbonate is important as a raw material for the production of an aromatic polycarbonate, which is the most widely used engineering plastics, without using toxic phosgene. As a process for producing an aromatic carbonate, a process of reacting an aromatic monohydroxy compound with phosgene has been known from long ago, and has also been the subject of a variety of studies in recent years. However, this process has the problem of using phosgene, and in addition chlorinated impurities that are difficult to separate out are present in the aromatic carbonate produced using this process, and hence this aromatic carbonate cannot be used as a raw material for the production of the aromatic polycarbonate. Because such chlorinated impurities markedly inhibit the polymerization reaction in the transesterification method which is carried out in the presence of an extremely small amount of a basic catalyst; for example, even if such chlorinated impurities are present in an amount of only 1 ppm, the polymerization hardly proceeds at all. To make the aromatic carbonate capable of using as a raw material of a transesterification method polycarbonate, a troublesome multi-stage separation/purification processes such as enough washing with a dilute aqueous alkaline solution and hot water, oil/water separation, distillation and so on are thus required. Furthermore, the yield of aromatic carbonate decreases due to hydrolysis loss and distillation loss during this separation/purification processes. Therefore, there are many problems in carrying out this method economically on an industrial scale.

On the other hand, a process for producing aromatic carbonates through transesterification reactions between a dialkyl carbonate and an aromatic monohydroxy compound is also known. However, such transesterification reactions are all equilibrium reactions. The equilibrium is biased extremely toward the original system and the reaction rate is slow, and hence there are many difficulties in producing aromatic carbonates industrially using this method. Two types of proposals have been made to improve on the above difficulties. These are developments of a catalyst to increase the reaction rate, and attempts to devise a reaction system so as to shift the equilibrium toward the product system as much as possible and thus improve the aromatic carbonate yield. For example, for the reaction between dimethyl carbonate and phenol, there have been proposed a process in which methanol produced as a by-product is distilled off by azeotropy together with an azeotrope-forming agent, a process in which the methanol produced as a by-product is removed by being adsorbed onto a molecular sieve, and a process in which, using an apparatus in which a distillation column is provided on top of a reactor, an alcohol produced as a by-product in the reaction is separated off from the reaction mixture, and at the same time unreacted starting material that evaporates is separated off by distillation (see Patent Document 1: examples in Japanese Patent Application Laid-Open No. 56-123948 (corresponding to U.S. Pat. No. 4,182,726)).

However, these reaction systems have basically been batch system or switchover system. Because there are limitations in the improvement of the reaction rate through catalyst development for such transesterification reactions, and the reaction rates are still slow, and thus it has been thought that the batch system is preferable to a continuous system. Of these, a continuous stirring tank reactor (CSTR) system in which a distillation column is provided on the top of the reactor has been proposed as the continuous system, but there are problems such as the reaction rate being slow, and a gas-liquid interface in the reactor being small, based on the volume of the liquid. Hence it is not possible to make the conversion high.

The present inventors have developed reactive distillation methods in which such a transesterification reaction is carried out in a continuous multi-stage distillation column simultaneously with separation by distillation, and have been the first in the world to disclose that such a reactive distillation system is useful for such a transesterification reaction, for example, a reactive distillation method in which a dialkyl carbonate and an aromatic hydroxy compound are continuously fed into the multi-stage distillation column, and the reaction is carried out continuously inside the column in which a catalyst is present, while continuously withdrawing a low boiling point component containing an alcohol produced as a by-product by distillation and continuously withdrawing a component containing a produced alkyl aryl carbonate from a lower portion of the column (see Patent Document 2: Japanese Patent Application Laid-Open No. 3-291257), a reactive distillation method in which an alkyl aryl carbonate is continuously fed into the multi-stage distillation column, and the reaction is carried out continuously inside the column in which a catalyst is present, while continuously withdrawing a low boiling point component containing a dialkyl carbonate produced as a by-product by distillation, and continuously withdrawing a component containing a produced diary carbonate from a lower portion of the column (see Patent document 3: Japanese Patent Application Laid-Open No. 4-9358), a reactive distillation method in which these reactions are carried out using two continuous multi-stage distillation columns, and hence a diaryl carbonate is produced continuously while efficiently recycling a dialkyl carbonate produced as a by-product (see Patent document 4: Japanese Patent Application Laid-Open No. 4-211038), and a reactive distillation method in which a dialkyl carbonate and an aromatic hydroxy compound or the like are continuously fed into the multi-stage distillation column, and a liquid that flows down through the column is withdrawn from a side outlet provided at an intermediate stage and/or a lowermost stage of the distillation column, and is introduced into a reactor provided outside the distillation column so as to bring about reaction, and is then introduced back through a circulating inlet provided at a stage above the stage where the outlet is provided, whereby reaction is carried out in both the reactor and the distillation column (see Patent Documents 5: Japanese Patent Application Laid-Open No. 4-224547; Patent Document 6: Japanese Patent Application Laid-Open No. 4-230242; Patent Document 7: Japanese Patent Application Laid-Open No. 4-235951).

These reactive distillation methods proposed by the present inventors are the first to enable aromatic carbonates to be produced continuously and efficiently, and many similar reactive distillation systems based on the above disclosures have been proposed thereafter (see Patent Document 8: International Publication No. 00/18720 (corresponding to U.S. Pat. No. 5,362,901); Patent Document 9: Italian Patent No. 01255746; Patent Document 10: Japanese Patent Application Laid-Open No. 6-9506 (corresponding to European Patent No. 0560159, and U.S. Pat. No. 5,282,965); Patent Document 11: Japanese Patent Application Laid-Open No. 6-41022 (corresponding to European Patent No. 0572870, and U.S. Pat. No. 5,362,901); Patent Documents 12: Japanese Patent Application Laid-Open No. 6-157424 (corresponding to European Patent No. 0582931, and U.S. Pat. No. 5,334,742); Patent Document 13: Japanese Patent Application Laid-Open No. 6-184058 (corresponding to European Patent No. 0582930, and U.S. Pat. No. 5,344,954); Patent Document 14: Japanese Patent Application Laid-Open No. 7-304713; Patent Document 15: Japanese Patent Application Laid-Open No. 9-40616; Patent Document 16: Japanese Patent Application Laid-Open No. 9-59225; Patent Document 17: Japanese Patent Application Laid-Open No. 9-110805; Patent Document 18: Japanese Patent Application Laid-Open No. 9-165357; Patent Document 19: Japanese Patent Application Laid-Open No. 9-173819; Patent Document 20: Japanese Patent Application Laid-Open No. 9-176094; Patent Document 21: Japanese Patent Application Laid-Open No. 2000-191596; Patent Document 22: Japanese Patent Application Laid-Open No. 2000-191597; Patent Document 23: Japanese Patent Application Laid-Open No. 9-194436 (corresponding to European Patent No. 0785184, and U.S. Pat. No. 5,705,673); Patent Document 24: International Publication No. 00/18720 (corresponding to U.S. Pat. No. 6,093,842); Patent Document 25: International Publication No. 01/042187 (corresponding to Published Japanese Translation of PCT Application No. 2003-516376); Patent Document 26: Japanese Patent Application Laid-Open No. 2001-64234; Patent Document 27: Japanese Patent Application Laid-Open No. 2001-64235; Patent Document 28: International Publication No. 02/40439 (corresponding to U.S. Pat. No. 6,596,894, U.S. Pat. No. 6,596,895, and U.S. Pat. No. 6,600,061)).

Among the reactive distillation systems, the present applicants have further proposed, as a method that enables highly pure aromatic carbonates to be produced stably for a prolonged period of time without a large amount of a catalyst being required, a method in which a high boiling point material containing a catalyst component is reacted with an active substance and then separated off, and the catalyst component is recycled (see Patent Document 29: International Publication No. 97/11049 (corresponding to European Patent No. 0855384, and U.S. Pat. No. 5,872,275)), and a method carried out while keeping the weight ratio of a polyhydric aromatic hydroxy compound in the reaction system to a catalyst metal at not more than 2.0 (see Patent Document 30: Japanese Patent Application Laid-Open No. 11-92429 (corresponding to European Patent No. 1016648, and U.S. Pat. No. 6,262, 210)). Furthermore, the present inventors have also proposed a method in which 70 to 99% by weight of phenol produced as a by-product in a polymerization process is used as a starting material, and diphenyl carbonate can be produced by means of the reactive distillation method. This diphenyl carbonate can be used as the raw material for polymerization to produce aromatic polycarbonates (see Patent Documents 31: Japanese Patent Application Laid-Open No. 9-255772 (corresponding to European Patent No. 0892001, and U.S. Pat. No. 5,747,609)).

As methods for separating a diaryl carbonate from the reaction mixture containing the diaryl carbonate that has been produced through transesterification reaction and the like between a dialkyl carbonate and an aromatic monohydroxy compound as a starting material as described above, and then purifying the diaryl carbonate, crystallization methods, distillation methods and the like have been proposed. With regard to the distillation methods, three methods have been proposed. One is a method in which the diaryl carbonate is obtained as a column top component from a distillation column; for example, there are:

I) a method in which the reaction mixture containing the catalyst is distilled as is in a batch type distillation column, and the diphenyl carbonate is obtained as the column top component (see Example 2 of Patent Document 10);

II) a method in which the reaction mixture containing the catalyst is subjected to flash evaporation, and thus separated into a high boiling point material containing most of the catalyst and a low boiling point material, and then the low boiling point material is distilled in a distillation column for starting material recovery, and a catalyst-containing diphenyl carbonate is obtained as a column bottom material, and then this column bottom material is distilled in a purifying column, whereby the diphenyl carbonate is obtained as a column top component (see Patent Document 33: Example 1 in Japanese Patent Application Laid-open No. 4-100824; Patent Document 34: Japanese Patent Application Laid-open No. 9-169704); and III) a method in which the reaction mixture containing the catalyst is distilled in a distillation column (or evaporator), and thus separated into a high boiling point material containing most of the catalyst and a low boiling point material, and then the low boiling point material is subjected to continuous sequential distillation using a distillation apparatus comprising three columns, i.e. a light fraction separating column, a methyl phenyl carbonate separating column, and a diphenyl carbonate separating column, whereby diphenyl carbonate is obtained as a column top component (see Patent Document 17).

Another is a method in which the diaryl carbonate is obtained as a column bottom component from a distillation column; for example, there is:

IV) a method in which the reaction mixture containing the catalyst is distilled in a distillation column, and thus separated into a high boiling point material containing most of the catalyst and a low boiling point material, and then the low boiling point material is distilled in a distillation column, and the diphenyl carbonate is obtained as a column bottom component (see Patent Document 26).

The other is a method in which the diaryl carbonate is obtained as a side cut component from a distillation column; for example, there are:

V) a method in which the reaction mixture containing the catalyst is introduced into a third reactive distillation column, and further reaction and distillation are carried out, whereby the diphenyl carbonate is obtained as a side cut component from the reactive distillation column (see Patent Documents 12 and 13);

VI) a method in which the reaction mixture containing the catalyst is subjected to flash evaporation, and thus separated into a high boiling point material containing most of the catalyst and a low boiling point material, and then the low boiling point material is introduced into a distillation column and distillation is carried out, whereby the diphenyl carbonate is obtained as a side cut component from the reactive distillation column (see Patent Documents 30 and 31; Patent Document 35: International Publication No. 92/18458 (corresponding to U.S. Pat. No. 5,426,207);

VII) a method in which the reaction mixture containing the catalyst is distilled in a first purifying column, and thus separated into a high boiling point material containing most of the catalyst and a low boiling point material, and then the low boiling point material is introduced into a second purifying column and distillation is carried out, whereby the diphenyl carbonate is obtained as a side cut component from the second purifying column (see Patent Document 36: Japanese Patent Application Laid-open No. 11-49727); and VIII) a method in which diphenyl carbonate containing phenyl salicylate is introduced into a distillation column having the number of theoretical stages being from 5 to 15, and distillation is carried out at a column bottom temperature of not less than 150° C., whereby the diphenyl carbonate is obtained as a side cut component from the distillation column (see Patent Document 32: Japanese Patent Application Laid-open No. 9-194437 (corresponding to European Patent No. 0784048)).

However, it has been shown that various problems remain with such diaryl carbonate separation/purification methods using these distillations. More specifically, the purity of the diphenyl carbonate obtained through the above 1) is low, and moreover this is a batch process and hence is not suitable for mass production on an industrial scale. Regarding the above 11), the method of Patent Document 33 is a batch method, and the diphenyl carbonate which was obtained through the method disclosed in Patent Document 34 contains a titanium catalyst, albeit in an amount of not more than 1 ppm, and hence is not suitable as a raw material for the production of a high-purity discolored polycarbonate. With the method of the above III), since the diphenyl carbonate is heated to a high temperature at the bottom of each of two of the distillation columns, i.e. the light fraction separating column and the methyl phenyl carbonate separating column, and is then subjected to a high temperature in the diphenyl carbonate separating column, the diphenyl carbonate is altered, bringing about a decrease in the purity and a decrease in the yield, which is undesirable. In actual fact, the diphenyl carbonate obtained in Example 1 in Patent Document 17 contains approximately 300 ppm of high boiling point by-products. The process of IV in which the diphenyl carbonate is obtained from the bottom of the column is unsuitable since the purity is low and hence a desired polycarbonate cannot be produced.

Since with the process of V, a reaction mixture containing all of the catalyst, unreacted starting material and impurities from the bottom of the second reactive distillation column is introduced into the third reactive distillation column from an upper portion thereof and the diphenyl carbonate is withdrawn from the side of the third reactive distillation column, vapor or mist of the starting material, the impurities, the catalyst or the like may thus be entrained, and hence the purity of the diphenyl carbonate obtained is low. The processes of VI and VII are preferable processes, but there is no mention of the presence of intermediate boiling point impurities having a boiling point between the alkyl aryl carbonate and the diaryl carbonate. Moreover, with the process of VIII, although it is stated that the content of phenyl salicylate is reduced from 3000 ppm to 50 ppm (Example 2 of Patent Document 32), nothing is mentioned whatsoever for other impurities. For example, even though the diphenyl carbonate is produced using the phosgene method in this example, and hence this is definitely a purification process for diphenyl carbonate containing chlorinated impurities, nothing is mentioned whatsoever with regard to the chlorinated impurities (which have an adverse effect on the polymerization to produce a polycarbonate and the properties of the polycarbonate even in an extremely small amount of only a few tens of ppb). With this process, such chlorinated impurities are not separated out sufficiently, and hence it is not be possible to use the diphenyl carbonate as a raw material for a polycarbonate. This is obvious from the fact that the chlorine content is 30 ppb in the diphenyl carbonate (in which after washing with alkaline hot water, and with hot water, and then water and the lower boiling point material is removed by distillation, the resulting diphenyl carbonate not containing water is purified by distillation) obtained in Comparative Example 1 of Patent Document 37 (Japanese Patent Application Laid-open No. 11-12230: this application was filed more than one year after Patent Document 32), which discloses the similar purifying method as the above process.

Furthermore, in Patent Document 32, the temperature and time at which phenol starts to be distilled off in the case that reaction is carried out with bisphenol A are given as a method of evaluating the purity of the diphenyl carbonate obtained through the distillation, but this test method cannot evaluate whether the diphenyl carbonate is suitable for polymerization. This is because even for diphenyl carbonate of low purity such that a polycarbonate of the required degree of polymerization cannot be produced, the initial reaction in which phenol is eliminated occurs sufficiently. Moreover, since with this evaluation method, a large amount of 2.3 ppm of NaOH based on the bisphenol A is used as a catalyst, even for diphenyl carbonate containing, for example, 1 ppm of chlorinated impurities, an incorrect evaluation that the diphenyl carbonate is of high purity and is suitable as a raw material for a polycarbonate would be obtained. As stated earlier, the diphenyl carbonate containing 1 ppm of chlorinated impurities cannot be used as the raw material for the polycarbonate at all. In ordinary polymerization, since such a large amount of an alkaline catalyst is not used, this evaluation method is not suitable for evaluating the purity of diphenyl carbonate to be used for producing polycarbonate. Further, in Patent Document 32, there is no specific description whatsoever of purification of diphenyl carbonate that has been obtained using the transesterification method. Since the types and contents of impurities differ between diphenyl carbonate obtained through the phosgene method and diphenyl carbonate obtained using the transesterification method, it cannot be said that diphenyl carbonate of the same purity will be obtained through the same purification method. It thus cannot be said at all that diphenyl carbonate having the required purity for the raw material of the polycarbonate would be obtained through the purification method of patent Document 32.

A reaction mixture obtained as a column bottom component by taking as a starting material a reaction mixture containing an alkyl aryl carbonate obtained through a transesterification reaction between a dialkyl carbonate and an aromatic monohydroxy compound, continuously feeding this starting material into a reactive distillation column comprising a continuous multi-stage distillation column in which a homogeneous catalyst is present, and carrying out a transesterification reaction and distillation simultaneously in the column generally contains small amounts of various reaction by-products in addition to the diaryl carbonate, the starting material and the catalyst. Such by-products are known to include by-products having a lower boiling point than that of the aromatic monohydroxy compound used as a starting material such as an alkyl aryl ether (e.g. anisole), and by-products having a higher boiling point than that of the diaryl carbonate such as an aryloxycarbonyl-(hydroxy)-arene (e.g. phenyl salicylate) and an aryloxycarbonyl-(aryloxycarboxyl)-arene, and processes for separating these out have been proposed. For example, processes for separating out anisole (see Patent Documents 16, 17 and 20), and processes for separating out phenyl salicylate (see Patent Documents 32 and 36) have been proposed.

By carrying out more detailed studies on processes for the continuous production of the diaryl carbonate, the present inventors have discovered that in addition to these publicly known impurities, intermediate boiling point by-products having a boiling point between the alkyl aryl carbonate and the diaryl carbonate are also present. Hitherto, there have been no documents whatsoever disclosing the presence of such intermediate boiling point by-products or a process for removing the same. When a diaryl carbonate for which the amounts of such intermediate boiling point by-products and high boiling point by-products have not been reduced down to a sufficient level is used as the raw material of a transesterification method polycarbonate, it has been discovered that these intermediate boiling point by-products and high boiling point by-products cause discoloration and a deterioration in the properties of the polycarbonate produced. It is thus necessary to reduce the amounts of both intermediate boiling point by-products and high boiling point by-products as much as possible.

DISCLOSURE OF INVENTION

It is an object of the present invention to provide a specific industrially useful process that enables a high-purity diaryl carbonate having low contents of intermediate boiling point and high boiling point impurities as required for producing a high-quality and high-performance polycarbonate to be produced stably for a prolonged period of time using as a starting material a reaction mixture containing an alkyl aryl carbonate obtained through a transesterification reaction between a dialkyl carbonate and an aromatic monohydroxy compound.

Since the present inventors disclosed a process for producing aromatic carbonates using a continuous multi-stage distillation column, various proposals regarding processes for the production of reaction mixtures containing aromatic carbonates by means of a reactive distillation method have been made. The present inventors have now carried out studies aimed at discovering a specific process enabling a high-purity diaryl carbonate that can be used as a raw material of a high-quality and high-performance polycarbonate to be continuously produced stably for a prolonged period of time from such a reaction mixture. As a result, the present inventors have reached to the present invention after discovering that the above object can be attained through a process in which separation by distillation is carried out using three distillation columns in a specified order. Moreover, the present inventors have discovered that it is particularly preferable if a reactive distillation column and the three distillation columns, each of which has a specified structure, and moreover the three distillation columns are each operated under specified distillation conditions.

That is, the present invention provides:
1. In a process for the production of a high-purity diaryl carbonate in which a diaryl carbonate is produced by taking as a starting material a reaction mixture containing an alkyl aryl carbonate that has been obtained through a transesterification reaction between a dialkyl carbonate and an aromatic monohydroxy compound, continuously feeding the starting material into a reactive distillation column comprising a continuous multi-stage distillation column in which a homogeneous catalyst is present, carrying out a transesterification reaction and distillation simultaneously in said column, continuously withdrawing a low boiling point reaction mixture containing a produced dialkyl carbonate from an upper portion of the column in a gaseous form, and continuously withdrawing a high boiling point reaction mixture containing a diaryl carbonate from a lower portion of the column in a liquid form, wherein the improvement comprises:

(a) said high boiling point reaction mixture is continuously introduced into a high boiling point material separating column A, and continuously subjected to separation by distillation into a column top component $A_T$ containing the diaryl carbonate and a column bottom component $A_B$ containing the catalyst and a high boiling point material;

(b) said column top component $A_T$ is continuously introduced into a diaryl carbonate purifying column B having a side cut outlet, and continuously subjected to separation by distillation into a column top component $B_T$, a side cut component $B_S$ and a column bottom component $B_B$, the high-purity diaryl carbonate being continuously withdrawn as the side cut component $B_S$; and (c) said column top component $B_T$ is continuously introduced into an intermediate boiling point material separating column C having a side cut outlet, and continuously subjected to separation by distillation into a column top component $C_T$ having said alkyl aryl carbonate as a main component thereof, a side cut component $C_S$ having as a main component thereof an intermediate boiling point material having a boiling point between that of said alkyl aryl carbonate and that of said diaryl carbonate, and a column bottom component $C_B$ having said diaryl carbonate as a main component thereof.

2. The process according to item 1, wherein said column top component $C_T$ from said intermediate boiling point material separating column C is continuously fed into said reactive distillation column.

3. The process according to item 1 or 2, wherein said column bottom component $C_B$ from said intermediate boiling point material separating column C is continuously fed into said high boiling point material separating column A.

4. The process according to any one of items 1 to 3, wherein said reactive distillation column is a continuous multi-stage distillation column comprising an internal with a number of stages n thereinside, n satisfying $10 \leq n \leq 80$.

5. The process according to any one of items 1 to 4, wherein said high boiling point material separating column A is a continuous multi-stage distillation column comprising an internal with a number of stages $n_A$ thereinside, $n_A$ satisfying $20 \leq n_A \leq 100$.

6. The process according to any one of items 1 to 5, wherein said diaryl carbonate purifying column B is a continuous multi-stage distillation column comprising an internal with a number of stages $n_B$ thereinside, $n_B$ satisfying $20 \leq n_B \leq 70$.

7. The process according to any one of items 1 to 6, wherein said intermediate boiling point material separating column C is a continuous multi-stage distillation column comprising an internal with a number of stages $n_C$ thereinside, $n_C$ satisfying $10 \leq n_C \leq 50$.

8. The process according to any one of items 1 to 7, wherein a distillation operation of said high boiling point material separating column A is carried out at a column bottom temperature $T_A$ in a range of from 185 to 280° C., and a column top pressure $P_A$ in a range of from 1000 to 20000 Pa.
9. The process according to any one of items 1 to 8, wherein a distillation operation of said diaryl carbonate purifying column B is carried out at a column bottom temperature $T_B$ in a range of from 185 to 280° C., and a column top pressure $P_B$ in a range of from 1000 to 20000 Pa.
10. The process according to any one of items 1 to 9, wherein a distillation operation of said intermediate boiling point material separating column C is carried out at a column bottom temperature $T_C$ in a range of from 150 to 280° C., and a column top pressure $P_C$ in a range of from 500 to 18000 Pa.
11. The process according to any one of items 1 to 10, wherein a reflux ratio for said high boiling point material separating column A is in a range of from 0.01 to 10.
12. The process according to any one of items 1 to 11, wherein a reflux ratio for said diaryl carbonate purifying column B is in a range of from 0.01 to 10.
13. The process according to any one of items 1 to 12, wherein a reflux ratio for said intermediate boiling point material separating column C is in a range of from 0.01 to 10.
14. A high-purity diphenyl carbonate obtained by the process according to any one of items 1 to 13, wherein the diphenyl carbonate is unsubstituted or substituted with a lower hydrocarbon, and has a halogen content of not more than 0.1 ppm, a content of said intermediate boiling point material of not more than 100 ppm, and a content of by-products having a higher boiling point than that of said diphenyl carbonate of not more than 100 ppm.
15. The high-purity diphenyl carbonate according to item 14, wherein the diphenyl carbonate is unsubstituted diphenyl carbonate, and the halogen content is not more than 10 ppb, the content of said intermediate boiling point material is not more than 30 ppm, and the content of each of phenyl salicylate, xanthone, phenyl methoxybenzoate, and 1-phenoxycarbonyl-2-phenoxycarboxy-phenylene, which are by-products having a higher boiling point than that of said diphenyl carbonate, is not more than 30 ppm.
16. The high-purity diphenyl carbonate according to item 15, wherein the content of said intermediate boiling point material is not more than 10 ppm, and the content of the by-products having a higher boiling point than that of said diphenyl carbonate is not more than 50 ppm.
17. The high-purity diphenyl carbonate according to item 16, wherein the halogen content is not more than 1 ppb, and the content of the by-products having a higher boiling point than that of the diphenyl carbonate is not more than 10 ppm.
18. A process for the production of an aromatic polycarbonate by transesterification with an aromatic dihydroxy compound, comprising using the high-purity diphenyl carbonate according to any one of items 14 to 17 as a raw material.
19. An aromatic polycarbonate obtained by transesterification between the high-purity diphenyl carbonate according to any one of items 14 to 17 and an aromatic dihydroxy compound.

ADVANTAGEOUS EFFECTS OF THE INVENTION

By implementing the present invention, a high-purity diaryl carbonate having low contents of intermediate boiling point and high boiling point impurities as required for producing a high-quality and high-performance polycarbonate can be produced stably for a prolonged period of time using as a starting material a reaction mixture containing an alkyl aryl carbonate obtained through a transesterification reaction between a dialkyl carbonate and an aromatic monohydroxy compound.

BEST MODE FOR CARRYING OUT THE INVENTION

Figure 1:
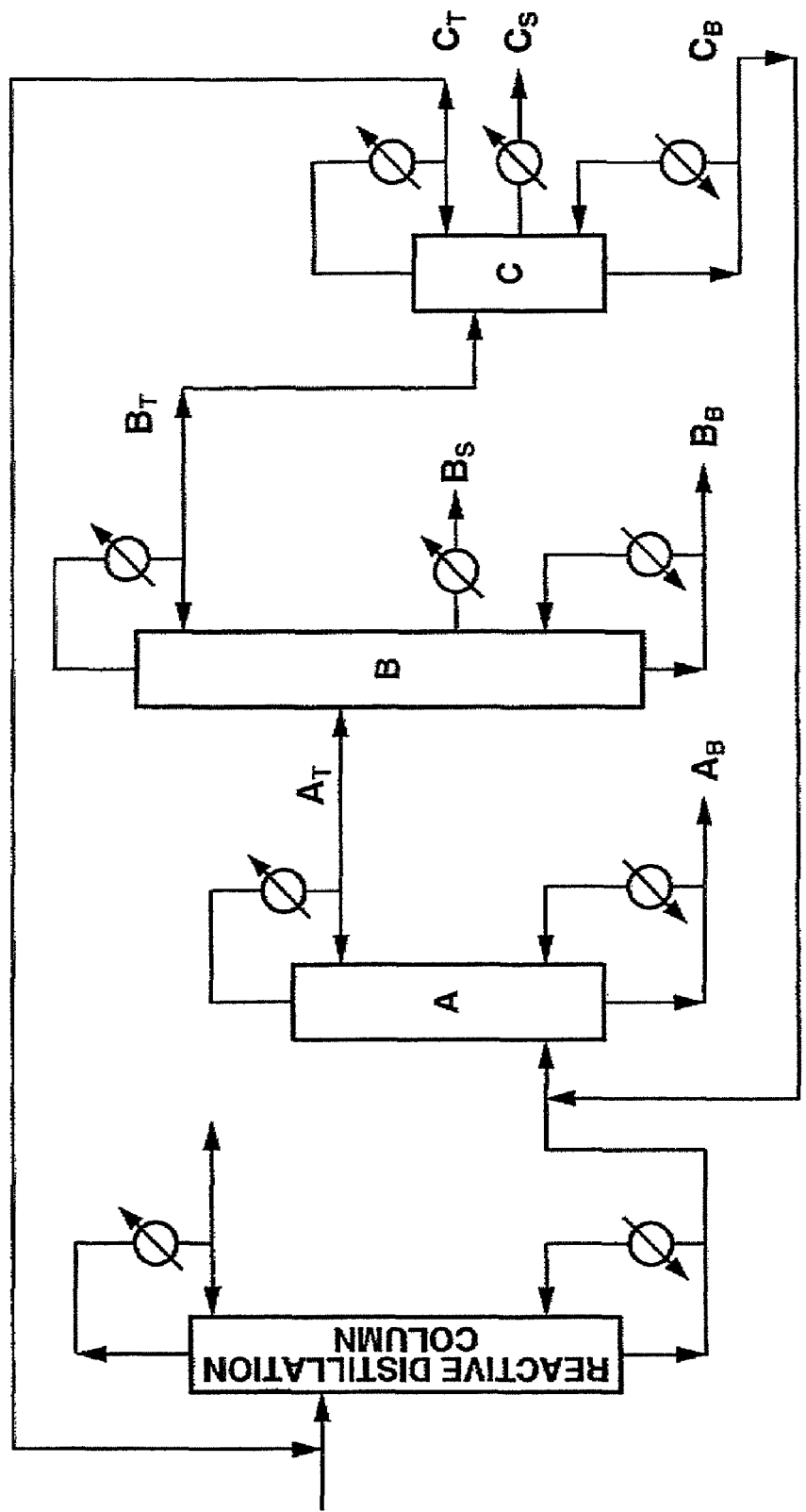
FIG. 1 is a schematic view of an apparatus for carrying out the present invention.
A: high boiling point material separating column, $A_T$: column top component of the high boiling point material separating column, $A_B$: column bottom component of the high boiling point material separating column, B: diaryl carbonate purifying column, $B_T$: column top component of the diaryl carbonate purifying column, $B_S$: side cut component of the diary carbonate purifying column, $B_B$: column bottom component of the diaryl carbonate purifying column, C: intermediate boiling point material separating column, $C_T$: column top component of the intermediate boiling point material separating column, $C_S$: side cut component of the intermediate boiling point material separating column, $C_B$: column bottom component of the intermediate boiling point material separating column.

In the following, the present invention is described in detail.
A dialkyl carbonate used in the present invention is a compound represented by the general formula (1);

$$R^1OCOOR^1 \qquad (1)$$

wherein $R^1$ represents an alkyl group having 1 to 10 carbon atoms, an alicyclic group having 3 to 10 carbon atoms, or an aralkyl group having 6 to 10 carbon atoms. Examples of $R^1$ include an alkyl group such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; an alicyclic group such as cyclopropyl, cyclobutyl, cyclopentyl, cyclohexyl and cycloheptyl; and an aralkyl group such as benzyl, phenethyl (isomers), phenylpropyl (isomers), phenylbutyl (isomers) and methylbenzyl (isomers). The above-mentioned alkyl groups, alicyclic group and aralkyl group may be substituted with other substituents such as lower alkyl group, a lower alkoxy group, a cyano group or a halogen atom, and may also contain an unsaturated bond therein.
Examples of dialkyl carbonates having such $R^1$ include dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers).
Of these dialkyl carbonates, ones preferably used in the present invention are dialkyl carbonates in which $R^1$ is an alkyl group having not more than four carbon atoms and not containing a halogen atom. A particularly preferable one is dimethyl carbonate. Moreover, of preferable dialkyl carbonates, particularly preferable ones are dialkyl carbonates produced in a state substantially not containing a halogen, for example ones produced from an alkylene carbonate substantially not containing a halogen and an alcohol substantially not containing a halogen.

An aromatic monohydroxy compound used in the present invention is a compound represented by undermentioned general formula (2). The type of the aromatic monohydroxy compound is not limited, so long as the hydroxyl group is directly bonded to the aromatic group;

$$Ar^1OH \quad (2)$$

wherein $Ar^1$ represents an aromatic group having 5 to 30 carbon atoms. Examples of aromatic monohydroxy compounds having such an $Ar^1$ include phenol; various alkylphenols such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols such as methoxyphenol (isomers) and ethoxyphenol (isomers); arylalkylphenols such as phenylpropylphenol (isomers); naphthol (isomers) and various substituted naphthols; and heteroaromatic monohydroxy compounds such as hydroxypyridine (isomers), hydroxycoumarin (isomers) and hydroxyquinoline (isomers).

Of these aromatic monohydroxy compounds, ones preferably used in the present invention are unsubstituted phenol and substituted phenols in which $Ar^1$ is an aromatic group having 6 to 10 carbon atoms. Unsubstituted phenol is particularly preferable. Moreover, of these aromatic monohydroxy compounds, ones substantially not containing a halogen are preferably used in the present invention.

The molar ratio of the dialkyl carbonate to the aromatic monohydroxy compound used for obtaining a reaction mixture containing an alkyl aryl carbonate that is the starting material in the present invention must be in a range of from 0.1 to 10. Outside this range, the amount of unreacted material remaining relative to the required amount of the alkyl aryl carbonate aimed for becomes high, which is not efficient, and moreover much energy is required to recover this unreacted material. For such reasons, the above molar ratio is preferable in a range of from 0.5 to 5, more preferably from 1 to 3.

A catalyst used in the present invention is a homogeneous catalyst which contains a metal such as Pb, Cu, Zn, Fe, Co, Ni, Al, Ti, V, Sn and the like, and which dissolves in the reaction system. A catalyst in which such a metallic component is bonded to organic groups can thus be preferably used. The catalyst component may of course have been reacted with an organic compound present in the reaction system such as aliphatic alcohols, aromatic monohydroxy compounds, alkyl phenyl carbonates, diphenyl carbonates or dialkyl carbonates, or may have been subjected to heating treatment with the starting material or products prior to the reaction. The catalyst used in the present invention is preferably one that has a high solubility in the reaction liquid under the reaction conditions. Examples of preferable catalysts in this sense include PbO, Pb(OH)$_2$ and Pb(OPh)$_2$; TiCl$_4$, Ti(OMe)$_4$, (MeO)Ti(OPh)$_3$, (MeO)$_2$Ti(OPh)$_2$, (MeO)$_3$Ti(OPh) and Ti(OPh)$_4$; SnCl$_4$, Sn(OPh)$_4$, Bu$_2$SnO and Bu$_2$Sn(OPh)$_2$; FeCl$_3$, Fe(OH)$_3$ and Fe(OPh)$_3$; and such catalysts that have been treated with aromatic monohydroxy compounds, the reaction liquid and the like.

In the present invention, it is particularly preferable to use a starting material and catalyst not containing a halogen. In this case, the diaryl carbonate produced does not contain a halogen at all, and hence it is important as a raw material when industrially producing a polycarbonate by means of a transesterification method. The reason for this is that if a halogen is present in the raw material for the polymerization in even an amount less than, for example, 1 ppm, then this halogen inhibits the polymerization reaction, and cause a deterioration in the properties of the polycarbonate produced, and cause discoloration of the polycarbonate.

The reaction mixture containing the alkyl aryl carbonate is produced through a transesterification reaction between the dialkyl carbonate and the aromatic monohydroxy compound (formula 3).

$$R^1OCOOR^1 + Ar^1OH \rightarrow Ar^1OCOOR^1 + R^1OH \quad (3)$$

The process for producing the reaction mixture containing the alkyl aryl carbonate may be any process, but one particularly preferable for industrial implementation is a process in which a continuous multi-stage distillation column is used as a reactive distillation column as previously proposed by the present inventors. A particularly preferable such process is one in which the transesterification reaction between the dialkyl carbonate and the aromatic monohydroxy compound is carried out in the presence of a homogeneous catalyst, and a reaction mixture containing an alcohol is continuously withdrawn from the top of the column, while the reaction mixture containing the alkyl aryl carbonate is continuously withdrawn from the bottom of the column.

In the present invention, the reaction mixture containing the alkyl aryl carbonate obtained in the above method is continuously fed into a reactive distillation column comprising a continuous multi-stage distillation column in which a homogeneous catalyst is present, a transesterification reaction and distillation are carried out simultaneously in the column, a low boiling point reaction mixture containing a produced dialkyl carbonate is continuously withdrawn from an upper portion of the column in a gaseous form, and a high boiling point reaction mixture containing a diaryl carbonate is continuously withdrawn from a lower portion of the column in a liquid form. Included under the transesterification reaction are a reaction in which the alkoxy group of the alkyl aryl carbonate is exchanged with the aryloxy group of the aromatic monohydroxy compound present in the system and an alcohol is eliminated (formula 4), and a reaction in which two molecules of the alkyl aryl carbonate are converted into the diaryl carbonate and the dialkyl carbonate through a transesterification reaction therebetween, i.e. a disproportionation reaction (formula 5). In the reactive distillation column of the present invention, it is mainly the disproportionation reaction of the alkyl aryl carbonate that occurs.

$$Ar^1OCOOR^1 + Ar^1OH \rightarrow Ar^1OCOOAr^1 + R^1OH \quad (4)$$

$$2Ar^1OCOOR^1 \rightarrow Ar^1OCOOAr^1 + R^1OCOOR^1 \quad (5)$$

Note that the reaction mixture containing the alkyl aryl carbonate used as the starting material in the present invention may be of high purity, or may contain other compounds, for example may contain the dialkyl carbonate and/or the aromatic monohydroxy compound used for obtaining the alkyl aryl carbonate, or may contain compounds or reaction by-products produced in this process and/or another processes, for example alcohols, alkyl aryl ethers, the diaryl carbonates, intermediate boiling point by-products, and/or high boiling point by-products. A process in which the reaction mixture obtained through the transesterification reaction between the dialkyl carbonate and the aromatic monohydroxy compound is taken as is as the starting material in the present invention without the unreacted materials and the catalyst being separated therefrom is also preferable. Moreover, in the case of industrial implementation as in the present invention, as the dialkyl carbonate and aromatic monohydroxy compound used for obtaining the reaction mixture containing the alkyl aryl carbonate that is taken as the starting material in the present invention, besides fresh dialkyl carbonate and aromatic monohydroxy compound newly introduced into the reaction system, it is also preferable to use dialkyl carbonate and aromatic monohydroxy compound recovered from this process and/or another processes.

The term "internal" used in the present invention means the part in a distillation column where gas and liquid are actually brought into contact with one another. The continuous multi-stage distillation column used as the reactive distillation column in the present invention is preferably a distillation column having a tray and/or a packing as the internal. The reaction between the alkyl aryl carbonate and the aromatic monohydroxy compound present in the system in the present invention has an extremely low equilibrium constant, and moreover the reaction rate is slow. Furthermore, the disproportionation reaction of the alkyl aryl carbonate that is the main reaction is also an equilibrium reaction, and has a low equilibrium constant, and a slow reaction rate. It has been discovered that a multi-stage distillation column having both the packing and the tray as the internal is particularly preferable as the continuous multi-stage distillation column used in the reactive distillation for carrying out these reactions in the present invention. It is yet more preferable for this distillation column to have a portion packed with the packing installed in the upper portion of the distillation column, and the tray portion installed in the lower portion of the distillation column. As the tray, for example, a bubble-cap tray, a sieve tray, a valve tray, a counterflow tray, a Superfrac tray, a Maxfrac tray or the like are preferable. As the packing, an irregular packing such as a Raschig ring, a Lessing ring, a Pall ring, a Berl saddle, an Intalox saddle, a Dixon packing, a McMahon packing or Heli-Pak or a structured packing such as Mellapak, Gempak, TECHNO-PAK, Flexipac, a Sulzer packing, Goodroll packing or a Grlitchgrid are preferable. Note that the term "number of stages (n) of the internal" used in the present invention means that the total number of trays in the case of a tray, and the theoretical number of stages in the case of the packing. Accordingly, in the case of the multi-stage column having both the tray portion and the portion packed with the packing, n means the sum of the total number of trays and the theoretical number of stages of the packing.

The reactive distillation column used in the present invention is preferably one having the internal with a number of stages n thereinside, n satisfying $10 \leq n \leq 80$. If n is less than 10, then the conversion decreases, and hence it is not possible to attain the desired production amount. Moreover, to keep down the equipment cost while securing the conversion enabling the desired production amount to be attained, n must be made to be not more than 80. Furthermore, if n is greater than 80, then the pressure difference between the top and bottom of the column becomes too great, and hence prolonged stable operation becomes difficult. Moreover, it becomes necessary to increase the temperature in the lower portion of the column, and hence side reactions become liable to occur, bringing about a decrease in the selectivity. A more preferable range for n is $15 \leq n \leq 60$, with $20 \leq n \leq 50$ being yet more preferable.

Moreover, in the present invention, a process in which a reflux operation of condensing a gaseous component withdrawn from the top of the reactive distillation column, and then returning some of this component into the upper portion of the distillation column is carried out is preferable. In this case, the reflux ratio is in a range of from 0.05 to 10, preferably 0.08 to 5, more preferably 0.1 to 2. In the present invention, when continuously feeding the starting material containing the alkyl aryl carbonate into the reactive distillation column, this starting material is preferably fed into the distillation column in a liquid form and/or a gaseous form from inlet(s) provided in one or a plurality of positions in the upper portion or a middle portion of the column below the gas outlet in the upper portion of the distillation column. Moreover, in the case of using a distillation column having the packing portion in the upper portion thereof and the tray portion in the lower portion thereof, which is a preferable embodiment in the present invention, it is preferable for at least one position where an inlet is installed to be between the packing portion and the tray portion. Moreover, in the case that the packing comprises a plurality of sets of structured packings, a process in which the inlet is installed in a space between the sets of the structured packings is preferable.

In the present invention, the method of making the homogeneous catalyst be present in the reactive distillation column may be any method, but it is preferable to feed the catalyst into the distillation column from a position above the middle portion of the distillation column. In this case, the catalyst liquid dissolved in the starting material or reaction liquid may be introduced into the column together with the starting material, or may be introduced into the column from a different inlet to the starting material. Moreover, if the transesterification reaction between the dialkyl carbonate and the aromatic monohydroxy compound is carried out using a homogeneous catalyst, then it is also preferable to use this catalyst as is; more of the same catalyst, or a different catalyst can be added as required. The amount of the catalyst used in the present invention varies depending on the type of the catalyst, the types and proportions of the starting material compounds, and reaction conditions such as the reaction temperature and the reaction pressure. The amount of the catalyst is generally in a range of from 0.0001 to 30% by weight, preferably from 0.005 to 10% by weight, more preferably from 0.001 to 1% by weight, based on the total weight of the starting material.

The reaction time for the transesterification reaction carried out in the present invention is considered to equate to the average residence time of the reaction liquid in the reactive distillation column. The reaction time varies depending on the form of the internal in the distillation column and the number of stages, the amount of the starting material fed into the column, the type and amount of the catalyst, the reaction conditions, and so on. The reaction time is generally in a range of from 0.01 to 10 hours, preferably 0.05 to 5 hours, more preferably 0.1 to 3 hours.

The reaction temperature varies depending on the type of the starting material compounds used, and the type and amount of the catalyst. The reaction temperature is generally in a range of from 100 to 350° C. It is preferable to increase the reaction temperature so as to increase the reaction rate. However, if the reaction temperature is too high, then side reactions become liable to occur, for example production of by-products such as Fries rearrangement products of the diaryl carbonate and an alkyl aryl ether, and ester compounds thereof increases, which is undesirable. For this reason, the reaction temperature is preferably in a range of from 130 to 280° C., more preferably 150 to 260° C., yet more preferably 180 to 240° C. Moreover, the reaction pressure varies depending on the type of the starting material compounds used and the composition of the starting material, the reaction temperature and so on. The reaction pressure may be any of a reduced pressure, normal pressure, or an applied pressure. The column top pressure is generally in a range of from 0.1 to $2\times10^7$ Pa, preferably $10^3$ to $10^6$ Pa, more preferably $5\times10^3$ to $10^5$ Pa.

The "selectivity" for the diaryl carbonate in the reactive distillation process in the present invention is based on the alkyl aryl carbonate reacted. In the present invention, a high selectivity of not less than 95% can generally be attained, preferably not less than 97%, more preferably not less than 99%.

In the reactive distillation process in the present invention, the low boiling point reaction mixture containing the produced dialkyl carbonate is continuously withdrawn from the upper portion of the column in a gaseous form, and the high boiling point reaction mixture containing the diaryl carbonate is continuously withdrawn from the lower portion of the column in a liquid form. The low boiling point reaction mixture may contain the alkyl aryl ether and the aromatic monohydroxy compound present in the system, unreacted alkyl aryl carbonate and so on. This low boiling point reaction mixture is preferably reused by recycling into the reactor in which the transesterification reaction between the dialkyl carbonate and the aromatic monohydroxy compound is carried out.

Moreover, the high boiling point reaction mixture may contain the aromatic monohydroxy compound, unreacted alkyl aryl carbonate, and in some cases small amounts of the dialkyl carbonate and the alkyl aryl ether and so on. Furthermore, this high boiling point reaction mixture may generally contain small amounts of other impurities and reaction by-products, for example, intermediate boiling point material having a boiling point between that of the alkyl aryl carbonate and that of the diaryl carbonate such as cresol, an alkoxycarbonyl-(hydroxy)-arene (e.g. methyl salicylate), an alkyl-(alkylaryl) carbonate (e.g. methyl cresyl carbonate), an alkoxycarbonyl-(alkoxycarboxyl)-arene (e.g. methyl methoxybenzoate), an alkoxyethyl-(aryl) carbonate (e.g. methoxyethyl-phenyl carbonate) and an alkylaryl-aryl ether (e.g. cresyl phenyl ether), and high boiling point material having a higher boiling point than that of the diaryl carbonate such as an aryloxycarbonyl-(hydroxy)-arene (e.g. phenyl salicylate), an alkoxycarbonyl-(aryloxy)-arene (e.g. methyl phenoxybenzoate), an alkylaryl-aryl carbonate (e.g. cresyl phenyl carbonate), xanthone and substituted xanthones, an aryloxycarbonyl-(alkoxy)-arene (e.g. phenyl methoxybenzoate), an aryloxycarbonyl-(aryloxy)-arene (e.g. phenyl phenoxybenzoate) and an aryloxycarbonyl-(aryloxycarboxyl)-arene (e.g. 1-phenoxycarbonyl-2-phenoxycarboxy-phenylene).

The compounds in brackets for the intermediate boiling point material and the high boiling point material described above are compounds that may be present in the high boiling point reaction mixture containing diphenyl carbonate continuously withdrawn from the lower portion of the reactive distillation column in the case of using as the starting material a reaction mixture containing methyl phenyl carbonate obtained through a transesterification reaction between dimethyl carbonate and phenol. Moreover, the cause of the production of a compound having an alkoxyethyl group is unclear, but this may be due to a 2-alkoxyethanol and/or 2-alkoxyethyl alkyl carbonate present in a small amount in the dialkyl carbonate by-produced in the case that the dialkyl carbonate is produced from ethylene carbonate and an alcohol.

However, the high boiling point by-products as above may be difficult to separate out, and with processes proposed hitherto, it has not been possible to reduce the amounts of such high boiling point by-products down to a sufficient level.

Moreover, regarding the intermediate boiling point by-products, in documents hitherto there has not even been any mention whatsoever of the existence thereof, and hence there have been no documents whatsoever disclosing or suggesting a process for separating out and thus removing such intermediate boiling point by-products. When producing the diaryl carbonate from the dialkyl carbonate and the aromatic monohydroxy compound, the present inventors have carried out prolonged continuous operation while recycling and thus reusing the starting material, and as a result have discovered that intermediate boiling point material and high boiling point material as above are by-produced, and accumulate in the system over time. The present inventors have also ascertained that if the diaryl carbonate for which the amounts of such intermediate boiling point material and high boiling point material have not been reduced down to a sufficient level is used as the raw material of a transesterification method polycarbonate, then these materials cause discoloration and deterioration in properties. An efficient process for reducing the amounts of both the intermediate boiling point by-products and high boiling point by-products down to a sufficient level is thus required. The process of the present invention attains this object.

In the present invention, the following must be carried out: the high boiling point reaction mixture containing the diaryl carbonate continuously withdrawn from the lower portion of the reactive distillation column is (a) continuously introduced into a high boiling point material separating column A, and continuously subjected to separation by distillation into a column top component ($A_T$) containing the diaryl carbonate and a column bottom component ($A_B$) containing the catalyst and a high boiling point material;

(b) the column top component ($A_T$) is continuously introduced into a diaryl carbonate purifying column B having a side cut outlet, and continuously subjected to separation by distillation into a column top component ($B_T$), a side cut component ($B_S$) and a column bottom component ($B_B$), high-purity diaryl carbonate being continuously withdrawn as the side cut component ($B_S$); and (c) the column top component ($B_T$) is continuously introduced into an intermediate boiling point material separating column C having a side cut outlet, and continuously subjected to separation by distillation into a column top component ($C_T$) having as a main component thereof the alkyl aryl carbonate, a side cut component ($C_S$) having as a main component thereof intermediate boiling point material having a boiling point between that of the alkyl aryl carbonate and that of the diaryl carbonate, and a column bottom component ($C_B$) having as a main component thereof the diaryl carbonate.

It is a characteristic feature of the present invention that the above processes (a), (b) and (c) are carried out in this order. This is because by carrying out these processes in this order, the heat history of the diaryl carbonate can be minimized, and as a result side reactions of the diaryl carbonate can be suppressed. With the process described in Patent Document 17 in which separation by distillation is carried out using three columns in order and the diaryl carbonate is obtained from the top of the third column, the heat history of the diaryl carbonate is great. In the present invention, it is more preferably to carry out the following:

(d) the column top component ($C_T$) is continuously fed into the reactive distillation column; and/or (e) the column bottom component ($C_B$) is continuously fed into the high boiling point material separating column A.

By carrying out the process(es) of (d) and/or (e) for recycling and thus reusing the column top component ($C_T$) and/or the column bottom component ($C_B$), the productivity for the high-purity diaryl carbonate can be improved, which is very important in the case of industrial implementation.

The high boiling point material separating column A used in the present invention is preferably a continuous multi-stage distillation column having an internal with a number of stages $n_A$ thereinside, $n_A$ satisfying $20 \leq n_A \leq 100$. The high boiling point material separating column A is preferably a distillation column having a tray and/or a packing as the internal.

If $n_A$ is less than 20, then the separation efficiency decreases and hence the desired high purity cannot be attained. Moreover, to keep down the equipment cost while attaining the desired separation efficiency, $n_A$ must be made to be not more than 100. Furthermore, if $n_A$ is greater than 100, then the pressure difference between the top and bottom of the column becomes too great, and hence prolonged stable operation of the high boiling point material separating column A becomes difficult. Moreover, it becomes necessary to increase the temperature in the lower portion of the column, and hence side reactions become liable to occur, which is undesirable. A more preferable range for $n_A$ is $30 \leq n_A \leq 70$, with $35 \leq n_A \leq 60$ being yet more preferable.

In the present invention, when continuously feeding the reaction mixture containing the diaryl carbonate into the high boiling point material separating column A, the inlet used may be in the upper portion, the middle portion or the lower portion of the column, but is preferably below the middle portion, particularly preferably in the lower portion of the column.

The distillation conditions for the high boiling point material separating column A are preferably a column bottom temperature ($T_A$) in a range of from 185 to 280° C., and a column top pressure ($P_A$) in a range of from 1000 to 20000 Pa.

It is undesirable for $T_A$ to be lower than 185° C., since then the column top pressure must be reduced, and hence equipment for maintaining a high vacuum must be used, and moreover the equipment increases in size. Moreover, it is undesirable for $T_A$ to be higher than 280° C., since then high boiling point by-products are produced during the distillation. A more preferable range for $T_A$ is from 190 to 240° C., with from 195 to 230° C. being yet more preferable.

It is undesirable for $P_A$ to be lower than 1000 Pa, since then large equipment enabling a high vacuum to be maintained must be used. Moreover, it is undesirable for $P_A$ to be higher than 20000 Pa, since then the distillation temperature must be increased and hence production of by-products increases. A more preferable range for $P_A$ is from 2000 to 15000 Pa, with from 3000 to 13000 Pa being yet more preferable.

Moreover, the reflux ratio for the high boiling point material separating column A is in a range of from 0.01 to 10, preferably from 0.08 to 5, more preferably from 0.1 to 3.

The diaryl carbonate purifying column B used in the present invention is preferably a continuous multi-stage distillation column having an internal with a number of stages $n_B$ thereinside, $n_B$ satisfying $20 \leq n_B \leq 70$. The diaryl carbonate purifying column B is preferably a distillation column having a tray and/or a packing as the internal. If $n_B$ is less than 20, then the separation efficiency for the column as a whole decreases and hence the desired high purity cannot be attained. Moreover, to keep down the equipment cost while attaining the desired separation efficiency, $n_B$ must be made to be not more than 70. Furthermore, if $n_B$ is greater than 70, then the pressure difference between the top and bottom of the column becomes too great, and hence prolonged stable operation of the diaryl carbonate purifying column B becomes difficult. Moreover, it becomes necessary to increase the temperature in the lower portion of the column, and hence side reactions become liable to occur, which is undesirable. A more preferable range for $n_B$ is $25 \leq n_B \leq 55$, with $30 \leq n_B \leq 50$ being yet more preferable. Moreover, the portion of the diaryl carbonate purifying column B below the side cut outlet must have the internals with not less than 3 stages, preferably from 3 to 15 stages, more preferably from 3 to 10 stages, installed therein.

In the present invention, when continuously feeding the column top component ($A_T$) from the high boiling point material separating column A into the diaryl carbonate purifying column B, the inlet used may be in the upper portion, the middle portion or the lower portion of the column, but is preferably in the middle portion above the side cut outlet. The portion of the diaryl carbonate purifying column B above this inlet preferably has the internals with not less than 5 stages, more preferably from 5 to 20 stages, yet more preferably from 7 to 15 stages, installed therein.

The distillation conditions for the diaryl carbonate purifying column B are preferably a column bottom temperature ($T_B$) in a range of from 185 to 280° C., and a column top pressure ($P_B$) in a range of from 1000 to 20000 Pa.

It is undesirable for $T_B$ to be lower than 185° C., since then the column top pressure must be reduced, and hence equipment for maintaining a high vacuum must be used, and moreover the equipment increases in size. Moreover, it is undesirable for $T_B$ to be higher than 280° C., since then high boiling point by-products are produced during the distillation. A more preferable range for $T_B$ is from 190 to 240° C., with from 195 to 230° C. being yet more preferable.

It is undesirable for $P_B$ to be lower than 1000 Pa, since then large equipment enabling a high vacuum to be maintained must be used. Moreover, it is undesirable for $P_B$ to be higher than 20000 Pa, since then the distillation temperature must be increased and hence production of by-products increases. A more preferable range for $P_B$ is from 2000 to 15000 Pa, with from 3000 to 13000 Pa being yet more preferable.

Moreover, the reflux ratio for the diaryl carbonate purifying column B is in a range of from 0.01 to 10, preferably from 0.1 to 8, more preferably from 0.5 to 5.

The intermediate boiling point material separating column C used in the present invention is preferably a continuous multi-stage distillation column having an internal with a number of stages $n_C$ thereinside, $n_C$ satisfying $10 \leq n_C \leq 50$. The intermediate boiling point material separating column C is preferably a distillation column having a tray and/or a packing as the internal. If $n_C$ is less than 10, then the separation efficiency for the column as a whole decreases and hence the desired high purity cannot be attained. Moreover, to keep down the equipment cost while attaining the desired separation efficiency, $n_C$ must be made to be not more than 50. Furthermore, if $n_C$ is greater than 50, then the pressure difference between the top and bottom of the column becomes too great, and hence prolonged stable operation of the intermediate boiling point material separating column C becomes difficult. Moreover, it becomes necessary to increase the temperature in the lower portion of the column, and hence side reactions become liable to occur, which is undesirable. A more preferable range for $n_C$ is $13 \leq n_C \leq 40$, with $16 \leq n_C \leq 30$ being yet more preferable. Moreover, the portion of the intermediate boiling point material separating column C below the side cut outlet must have the internals with not less than 3 stages, preferably from 4 to 15 stages, more preferably from 5 to 10 stages, installed therein.

In the present invention, when continuously feeding the column top component ($B_T$) from the diaryl carbonate purifying column B into the intermediate boiling point material separating column C, the inlet used may be in the upper portion, the middle portion or the lower portion of the column, but is preferably in the middle portion above the side cut outlet. The portion of the intermediate boiling point material separating column C above this inlet preferably has the internals with not less than 3 stages, more preferably from 4 to 15 stages, yet more preferably from 5 to 10 stages, installed therein.

The distillation conditions for the intermediate boiling point material separating column C are preferably a column bottom temperature ($T_C$) in a range of from 150 to 280° C., and a column top pressure ($P_C$) in a range of from 500 to 18000 Pa.

It is undesirable for $T_C$ to be lower than 150° C., since then the column top pressure must be reduced, and hence equipment for maintaining a high vacuum must be used, and moreover the equipment increases in size. Moreover, it is undesirable for $T_C$ to be higher than 280° C., since then high boiling point by-products are produced during the distillation. A more preferable range for $T_C$ is from 160 to 240° C., with from 165 to 230° C. being yet more preferable.

It is undesirable for $P_C$ to be lower than 500 Pa, since then large equipment enabling a high vacuum to be maintained must be used. Moreover, it is undesirable for $P_C$ to be higher than 18000 Pa, since then the distillation temperature must be increased and hence production of by-products increases. A more preferable range for $P_C$ is from 800 to 15000 Pa, with from 1000 to 13000 Pa being yet more preferable.

Moreover, the reflux ratio for the intermediate boiling point material separating column C is in a range of from 0.01 to 10, preferably from 0.1 to 5, more preferably from 0.2 to 2.

In the present invention, the high boiling point reaction mixture continuously withdrawn from the bottom of the reactive distillation column is preferably fed into the high boiling point material separating column A. This high boiling point reaction mixture generally contains 0.05 to 2% by weight of the dialkyl carbonate, 0.1 to 20% by weight of the aromatic monohydroxy compound, 0.02 to 2% by weight of an alkyl aryl ether, 10 to 45% by weight of the alkyl aryl carbonate, 50 to 80% by weight of the diaryl carbonate, 0.01 to 1% by weight of intermediate boiling point by-products, 0.1 to 5% by weight of high boiling point by-products, and 0.001 to 5% by weight of the catalyst. The composition of the high boiling point reaction mixture varies depending on the reactive distillation conditions, the type and amount of the catalyst and so on, but so long as the reactive distillation is carried out under constant conditions, a reaction mixture of approximately constant composition can be produced, and hence the composition of the high boiling point reaction mixture fed into the high boiling point material separating column A may be approximately constant. Nevertheless, in the present invention, so long as the composition of the high boiling point reaction mixture is within the above range, then even if this composition fluctuates somewhat, the separation can still be carried out with approximately the same separation efficiency. This is one of the characteristic features of the present invention.

In the present invention, when continuously feeding the high boiling point reaction mixture into the high boiling point material separating column A, the high boiling point reaction mixture may be fed in as a liquid from inlet(s) provided in one or a plurality of positions below the middle portion of the separating column A, or it is also preferable to feed the high boiling point reaction mixture into the column via a reboiler of the separating column A from piping provided at a lower portion of the reboiler. The amount of the high boiling point reaction mixture fed into the high boiling point material separating column A varies depending on the amount of the high-purity diaryl carbonate to be produced, the concentration of the diaryl carbonate in the high boiling point reaction mixture, the separation conditions for the separating column A and so on.

The high boiling point reaction mixture continuously fed into the high boiling point material separating column A is separated into a column top component ($A_T$) containing most of the diaryl carbonate, most of compounds having a lower boiling point than that of the diaryl carbonate such as unreacted starting material, an alkyl aryl ether, the alkyl aryl carbonate and intermediate boiling point material, and a very small amount of high boiling point by-products, and a column bottom component ($A_B$) containing a small amount of the diary carbonate, the catalyst, and most of by-products having a higher boiling point than that of the diaryl carbonate. The column bottom component ($A_B$) may contain small amounts of the aromatic monohydroxy compound, the alkyl aryl carbonate and the intermediate boiling point by-products. Such organic material in the column bottom component ($A_B$) plays a useful role in dissolving the catalyst component and thus maintaining a liquid state. It is generally preferable for all or some of the column bottom component ($A_B$) to be reused by recycling into the reactor in which the transesterification reaction between the dialkyl carbonate and the aromatic monohydroxy compound is carried out and/or the reactive distillation column of the present invention as a transesterification reaction catalyst component.

In the present invention, in the case, for example, of using unsubstituted phenol or a lower hydrocarbon-substituted phenol as the aromatic monohydroxy compound, the catalyst component and by-products having a higher boiling point than that of diphenyl carbonate such as phenyl salicylate, xanthone, a phenyl alkoxybenzoate and 1-phenoxycarbonyl-2-phenoxycarboxy-phenylene or by-products having a higher boiling point than that of the lower hydrocarbon-substituted diphenyl carbonate such as lower hydrocarbon-substituted derivatives of the above compounds are almost completely separated out as the column bottom component ($A_B$) in the high boiling point material separating column A.

It is a characteristic feature of the present invention that it is easy to make the content of the catalyst component and the by-products having a higher boiling point than that of the diaryl carbonate in the column top component ($A_T$) be generally not more than 200 ppm, preferably not more than 100 ppm, more preferably not more than 50 ppm. It is another characteristic feature of the present invention that despite making the column top component ($A_T$) hardly contain any such high boiling point by-products, most of the diaryl carbonate in the reaction mixture introduced can be withdrawn from the top of the column. In the present invention, not less than 95%, preferably not less than 96%, more preferably not less than 98%, of the diaryl carbonate in the reaction mixture continuously fed into the high boiling point material separating column A can be withdrawn from the top of the column.

Moreover, in the present invention, although dependent on the composition of the reaction mixture fed into the separating column A, in general 90 to 97% by weight of the liquid continuously fed in is continuously withdrawn from the top of the column as the column top component ($A_T$), with 10 to 3% by weight being continuously withdrawn from the bottom of the column as the column bottom component ($A_B$). The composition of the column top component ($A_T$) is generally 0.05 to 2% by weight of the dialkyl carbonate, 1 to 21% by weight of the aromatic monohydroxy compound, 0.05 to 2% by weight of an alkyl aryl ether, 11 to 47% by weight of the alkyl aryl carbonate, 0.05 to 1% by weight of intermediate boiling point by-products, and 52 to 84% by weight of the diaryl carbonate; the content of high boiling point by-products is generally not more than 200 ppm, preferably not more than 100 ppm, more preferably not more than 50 ppm.

As stated above, an amount of the column top component ($A_T$) continuously withdrawn from the top of the high boiling point material separating column A is generally approximately 90 to 97% of the reaction mixture fed into the separating column A. This column top component ($A_T$) is continuously fed as is into the diaryl carbonate purifying column B from an inlet provided at a middle portion of the purifying column B, and is continuously separated into three components, i.e. a column top component ($B_T$), a side cut component ($B_S$), and a column bottom component ($B_B$). All of components having a lower boiling point than that of the diaryl carbonate contained in the column top component ($A_T$) from the separating column A fed into the purifying column B are continuously withdrawn from the top of the purifying column B as the column top component ($B_T$), and a small amount of liquid is continuously withdrawn from the bottom of the purifying column B. A small amount of the diaryl carbonate is contained in the column top component ($B_T$), this amount generally being from 1 to 9%, preferably from 3 to 8%, of the diaryl carbonate fed in.

The column bottom component ($B_B$) from the diaryl carbonate purifying column B comprises the diaryl carbonate, and a small amount of high boiling point by-products concentrated to approximately a few percent. Another characteristic feature of the present invention is that the amount of the diaryl carbonate in the column bottom component ($B_B$) withdrawn from the bottom of the purifying column B can be kept very low. This amount is generally from 0.05 to 0.5% of the diaryl carbonate fed in.

A high-purity diaryl carbonate is continuously withdrawn from the side cut outlet of the diaryl carbonate purifying column B, the amount thereof generally corresponding to approximately 90 to 96% of the diaryl carbonate fed into the purifying column B. The purity of the diaryl carbonate obtained as the side cut component ($B_S$) in the present invention is generally not less than 99.9%, preferably not less than 99.99%, more preferably not less than 99.999%. The content of intermediate boiling point by-products having a boiling point between that of the alkyl aryl carbonate and that of the diaryl carbonate is not more than 100 ppm, preferably not more than 30 ppm, more preferably not more than 10 ppm, or it may even be possible to make the side cut component ($B_S$) substantially not contain such intermediate boiling point by-products at all. Moreover, the content of high boiling point by-products having a higher boiling point than that of the diaryl carbonate is not more than 100 ppm, preferably not more than 50 ppm, more preferably not more than 10 ppm.

The contents of high boiling point impurities in the diaryl carbonate obtained when carrying out the present invention using an alkyl aryl carbonate obtained through a transesterification reaction between a dialkyl carbonate and phenol or a lower hydrocarbon-substituted phenol are not more than 30 ppm, preferably not more than 10 ppm, more preferably not more than 1 ppm for phenyl salicylate or a lower hydrocarbon-substituted derivative thereof, not more than 30 ppm, preferably not more than 10 ppm, more preferably not more than 1 ppm for xanthone, not more than 30 ppm, preferably not more than 10 ppm, more preferably not more than 1 ppm for phenyl methoxybenzoate or a lower hydrocarbon-substituted derivative thereof, and not more than 30 ppm, preferably not more than 10 ppm, more preferably not more than 5 ppm for 1-phenoxycarbonyl-2-phenoxycarboxy-phenylene or a lower hydrocarbon-substituted derivative thereof. Moreover, the total content of these high boiling point by-products is not more than 100 ppm, preferably not more than 50 ppm, more preferably not more than 10 ppm.

Moreover, in the present invention, a starting material and catalyst not containing a halogen are generally used, and hence the halogen content of the diaryl carbonate obtained is not more than 0.1 ppm, preferably not more than 10 ppb, more preferably not more than 1 ppb.

The column top component ($B_T$) continuously withdrawn from the top of the diaryl carbonate purifying column B is continuously fed as is into the intermediate boiling point material separating column C from an inlet provided at a middle portion of the separating column C, and is continuously separated into three components, i.e. a column top component ($C_T$), a side cut component ($C_S$), and a column bottom component ($C_B$). The composition of the column top component ($B_T$) from the diaryl carbonate purifying column B is generally 0.05 to 2% by weight of the dialkyl carbonate, 1 to 20% by weight of the aromatic monohydroxy compound, 0.05 to 2% by weight of an alkyl aryl ether, 60 to 95% by weight of the alkyl aryl carbonate, 0.05 to 2% by weight of intermediate boiling point by-products, and 0.1 to 15% by weight of the diaryl carbonate; the content of high boiling point by-products is generally not more than 500 ppm, preferably not more than 300 ppm.

An amount of the column top component ($C_T$) from the intermediate boiling point material separating column C is generally 80 to 97% by weight of the column top component ($B_T$) fed in. The composition of the column top component ($C_T$) is generally 0.1 to 2% by weight of the dialkyl carbonate, 1 to 20% by weight of the aromatic monohydroxy compound, 0.05 to 2% by weight of an alkyl aryl ether, 60 to 95% by weight of the alkyl aryl carbonate, and 0.05 to 0.5% by weight of intermediate boiling point by-products; the content of the diaryl carbonate and high boiling point by-products is generally not more than 100 ppm, preferably not more than 10 ppm.

An amount of the side cut component ($C_S$) from the intermediate boiling point material separating column C is generally 1 to 10% by weight of the column top component ($B_T$) fed in. The composition of the side cut component ($C_S$) is generally 0.01 to 5% by weight of the aromatic monohydroxy compound, not more than 10 ppm of an alkyl aryl ether, 10 to 50% by weight of the alkyl aryl carbonate, 10 to 70% by weight of intermediate boiling point by-products, 5 to 60% by weight of the diaryl carbonate, and not more than 1% by weight of high boiling point by-products.

An amount of the column bottom component ($C_B$) from the intermediate boiling point material separating column C is generally 3 to 15% by weight of the column top component ($B_T$) fed in. The composition of the column bottom component ($C_B$) is generally 0.01 to 0.5% by weight of the aromatic monohydroxy compound, not more than 10 ppm of an alkyl aryl ether, 0 to 3% by weight of the alkyl aryl carbonate, 0 to 0.1% by weight of intermediate boiling point by-products, 95 to 99.9% by weight of the diaryl carbonate, and not more than 1% by weight of high boiling point by-products.

It is preferable for some or all the column top component ($C_T$) separated off by the intermediate boiling point material separating column C as described above to be taken as starting material for the initial transesterification reaction and/or the reactive distillation of the present invention. The column top component ($C_T$) has low contents of the intermediate boiling point by-products and high boiling point by-products, and has a high content of the alkyl aryl carbonate, and hence in the present invention, it is particularly preferable to continuously feed the column top component ($C_T$) into the reactive distillation column in which the disproportionation reaction mainly occurs. Such reuse by recycling is particularly important in the case of industrial implementation.

Moreover, it is also preferable to recycling and thus reuse some or all of the column bottom component ($C_B$) separated off as described above. The column bottom component ($C_B$) has low contents of the intermediate boiling point by-products and high boiling point by-products, and has a high content of the diaryl carbonate, and hence is preferably recovered. Although the column bottom component ($C_B$) can also be continuously fed into the diaryl carbonate purifying column B, it is particularly preferable to continuously feed the column bottom component ($C_B$) into the high boiling point material separating column A, since then the high-purity diaryl carbonate can be obtained with yet higher productivity. Such reuse by recycling is particularly important in the case of industrial implementation.

The term "prolonged stable operation" used in the present invention means that operation can be carried out continuously in a steady state based on the operating conditions with no reaction abnormalities, distillation abnormalities such as flooding, clogging of piping, or erosion for not less than 1000 hours, preferably not less than 3000 hours, more preferably not less than 5000 hours, and a predetermined amount of the high-purity diaryl carbonate can be produced while maintaining high selectivity.

In the case of carrying out the present invention using an alkyl aryl carbonate obtained through a transesterification reaction between a dialkyl carbonate and phenol or a lower hydrocarbon-substituted phenol, the content of intermediate boiling point by-products contained in the unsubstituted or lower hydrocarbon-substituted diphenyl carbonate obtained is not more than 100 ppm, preferably not more than 30 ppm, more preferably not more than 10 ppm, yet more preferably not more than 1 ppm, and the contents of high boiling point impurities are not more than 30 ppm, preferably not more than 10 ppm, more preferably not more than 1 ppm for phenyl salicylate or a lower hydrocarbon-substituted derivative thereof, not more than 30 ppm, preferably not more than 10 ppm, more preferably not more than 1 ppm for xanthone, not more than 30 ppm, preferably not more than 10 ppm, more preferably not more than 1 ppm for phenyl methoxybenzoate or a lower hydrocarbon-substituted derivative thereof, and not more than 30 ppm, preferably not more than 10 ppm, more preferably not more than 5 ppm for 1-phenoxycarbonyl-2-phenoxycarboxy-phenylene or a lower hydrocarbon-substituted derivative thereof. Moreover, the total content of these high boiling point by-products is not more than 100 ppm, preferably not more than 50 ppm, more preferably not more than 10 ppm.

Moreover, in the present invention, a dialkyl carbonate, phenol or lower hydrocarbon-substituted phenol, and catalyst each not containing a halogen are generally used, and hence the halogen content of the unsubstituted or lower hydrocarbon-substituted diphenyl carbonate obtained is not more than 0.1 ppm, preferably not more than 10 ppb, more preferably not more than 1 ppb.

The diaryl carbonate obtained in the present invention is of very high purity, and hence is particularly preferably used as a raw material for the production of an aromatic polycarbonate through transesterification with an aromatic dihydroxy compound.

Furthermore, an aromatic polycarbonate using as a raw material thereof a high-purity diphenyl carbonate obtained through the present invention is uncolored and of high purity and high performance, and hence can be preferably used as an optical disk which is a recording medium for information, music, images and so on, or as any of various engineering plastics. A process for the production of an aromatic polycarbonate through transesterification between the high-purity diphenyl carbonate of the present invention and an aromatic dihydroxy compound may be any process, but a particularly preferable process that makes good use of the properties of the high-purity diphenyl carbonate of the present invention is a process proposed by the present inventors in which polymerization is carried out while making a molten prepolymer drop down along a guide fixed in space (see, for example, WO 99/64492).

The material constituting the reactive distillation column, the high boiling point material separating column A, the diaryl carbonate purifying column B, the intermediate boiling point material separating column C, and other liquid-contacting parts used in the present invention is generally a metallic material such as carbon steel or stainless steel. In terms of the quality of the diaryl carbonate produced, stainless steel is preferable.

EXAMPLES

Hereinbelow, the present invention will be described in more detail with reference to the following Examples, but the present invention is not limited to the following Examples. The purity of the diphenyl carbonate, and the contents of impurities were measured by means of a gas chromatography method, and the halogen content was measured by means of an ion chromatography method.

Example 1

Diphenyl carbonate was produced using an apparatus comprising a reactive distillation column (height: 6 m, diameter: 10 inches, internal: sieve tray, number of stages: 20), a high boiling point material separating column A (height: 5 m, diameter: 6 inches, internal: Dixon packing, theoretical number of stages: 25), a diaryl carbonate purifying column B (height: 8 m, diameter: 6 inches, internal: sieve tray, number of stages: 30) and an intermediate boiling point material separating column C (height: 4 m, diameter: 2 inches, internal: Dixon packing, theoretical number of stages: 15) as shown in FIG. 1.

A reaction mixture containing 18.7% by weight of methyl phenyl carbonate that had been obtained by subjecting phenol and dimethyl carbonate containing anisole to a transesterification reaction was used as a starting material. This starting material contained 27.5% by weight of dimethyl carbonate, 8.2% by weight of anisole, 43.9% by weight of phenol, 1.5% by weight of diphenyl carbonate, 0.1% by weight of intermediate boiling point by-products, and 110 ppm of high boiling point by-products, and further contained approximately 100 ppm of Pb(OPh)$_2$ as a catalyst. The starting material substantially did not contain halogens (lower than the detection limit for the ion chromatography, i.e. 1 ppb or less).

The starting material was continuously fed into the reactive distillation column at 30 kg/hr from a position 2 m below the top of the column, whereby reactive distillation was carried out. The reactive distillation was carried out continuously under conditions of a column bottom temperature in the reactive distillation column being 205° C., a column top pressure being 39000 Pa, and a reflux ratio being 0.3. A high boiling point reaction mixture containing diphenyl carbonate was continuously withdrawn from the bottom of the column, and was continuously fed into a lower portion of the high boiling point material separating column A. Separation by distillation was carried out continuously under conditions of a column bottom temperature in the high boiling point material separating column A being 205° C., a column top pressure being 1900 Pa, and a reflux ratio being 0.6. A column top component ($A_T$) continuously withdrawn from the top of the high boiling point material separating column A was continuously fed into the diaryl carbonate purifying column B from a position 2 m below the top of the diaryl carbonate purifying column B. Separation by distillation was carried out continuously under conditions of a column bottom temperature in the diaryl carbonate purifying column B being 208° C., a column top pressure being 5000 Pa, and a reflux ratio being 1.99. Diphenyl carbonate was continuously withdrawn from a side cut outlet installed in a position 1.5 m above the bottom of the purifying column B.

A column top component ($B_T$) continuously withdrawn from the top of the diaryl carbonate purifying column B was continuously fed into the intermediate boiling point material separating column C from a position 1 m below the top of the intermediate boiling point material separating column C. Separation by distillation was carried out continuously under conditions of a column bottom temperature in the intermediate boiling point material separating column C being 170° C., a column top pressure being 4800 Pa, and a reflux ratio being 0.44. Intermediate boiling point material having intermediate boiling point by-products as a main component thereof was continuously withdrawn from a side cut outlet installed in a position 1 m above the bottom of the intermediate boiling point material separating column C. A column top component ($C_T$) continuously withdrawn from the top of the intermediate boiling point material separating column C was recycled and thus reused by being continuously fed as is into the reactive distillation column. A column bottom component ($C_B$) continuously withdrawn from the bottom of the intermediate boiling point material separating column C was recycled and thus reused by being continuously fed as is into the lower portion of the high boiling point material separating column A.

When all of the distillation columns had reached a stable steady state, the flow rate for the starting material fed into the reactive distillation column was 30 kg/hr for the fresh starting material and 1.2 kg/hr for the column top component ($C_T$) from the intermediate boiling point material separating column C that was recycled and thus reused, i.e. 31.2 kg/hr in total. The flow rate for the high boiling point reaction mixture continuously withdrawn from the bottom of the reactive distillation column was 3.6 kg/hr, and the composition thereof was 0.1% by weight of dimethyl carbonate, 0.05% by weight of anisole, 1.2% by weight of phenol, 29.5% by weight of methyl phenyl carbonate, 68.0% by weight of diphenyl carbonate, 0.25% by weight of intermediate boiling point by-products, and 0.9% by weight of high boiling point by-products including the catalyst.

The flow rate for the material fed into the high boiling point material separating column A was 3.6 kg/hr for the above high boiling point reaction mixture and 0.4 kg/hr for the column bottom component ($C_B$) from the intermediate boiling point material separating column C that was recycled and thus reused, i.e. 4.0 kg/hr in total. The flow rate for the column top component ($A_T$) continuously withdrawn from the top of the high boiling point material separating column A was 3.8 kg/hr. The flow rate for the column top component ($B_T$) continuously withdrawn from the diaryl carbonate purifying column B was 1.62 kg/hr, the flow rate for the column bottom component ($B_B$) was 0.08 kg/hr, and the flow rate for the side cut component ($B_S$) was 2.1 kg/hr. The flow rate for the column top component ($C_T$) continuously withdrawn from the intermediate boiling point material separating column C was 1.2 kg/hr, the flow rate for the column bottom component ($C_B$) was 0.4 kg/hr, and the flow rate for the side cut component ($C_S$) was 0.02 kg/hr.

The composition of the side cut component ($C_S$) from the intermediate boiling point material separating column C was 0.7% by weight of phenol, 24.3% by weight of methyl phenyl carbonate, a total of 37.6% by weight of intermediate boiling point by-products (34.2% by weight of methyl methoxybenzoate, 3.2% by weight of 2-methoxyethyl-phenyl carbonate, and 0.2% by weight of cresyl phenyl ether), 38.8% by weight of diphenyl carbonate, and 0.3% by weight of high boiling point by-products, and hence the intermediate boiling point by-products were concentrated therein. The column top component ($C_T$) from the intermediate boiling point material separating column C contained 8.5% by weight of phenol, and 90.5% by weight of methyl phenyl carbonate. The column bottom component ($C_B$) from the intermediate boiling point material separating column C contained 1.8% by weight of methyl phenyl carbonate, and 97.2% by weight of diphenyl carbonate.

The content of diphenyl carbonate in the side cut component ($B_S$) from the diaryl carbonate purifying column B was at least 99.999% by weight, and each of intermediate boiling point by-products and high boiling point by-products were undetectable, the content thereof being not more than 1 ppm. Moreover, the halogen content of the diphenyl carbonate was undetectable, the content thereof being not more than 1 ppb.

It was possible to continuously carry out the above reactive distillation and separation/purification by distillation stably for 5000 hours; the analytical values after 500 hours, 1000 hours, 3000 hours, and 5000 hours were each approximately the same as above, and hence it was possible to stably obtain high-purity diphenyl carbonate substantially not containing intermediate boiling point by-products or high boiling point by-products.

Comparative Example 1

Reactive distillation and separation/purification by distillation were carried out using the same process as in Example 1, except that the intermediate boiling point material separating column C was not used, but rather the column top component ($B_T$) from the diaryl carbonate purifying column B was reused by recycling into the reactive distillation column. Up to the elapse of 50 hours, diphenyl carbonate was obtained with approximately the same results as in Example 1, but the content of intermediate boiling point by-products such as methyl methoxybenzoate and 2-methoxyethyl-phenyl carbonate then increased continuously, being 10 ppm after 100 hours, 25 ppm after 200 hours, and 40 ppm after 300 hours.

Example 2

Reactive distillation and separation/purification by distillation were carried out using the same process as in Example 1, except that the conditions for the separation/purification by distillation were changed to a column bottom temperature of 210° C., a column top pressure of 3800 Pa, and a reflux ratio of 0.61 for the high boiling point material separating column A, a column bottom temperature of 220° C., a column top pressure of 6700 Pa, and a reflux ratio of 1.5 for the diaryl carbonate purifying column B, and a column bottom temperature of 200° C., a column top pressure of 2400 Pa, and a reflux ratio of 0.35 for the intermediate boiling point material separating column C. The purity of the diphenyl carbonate after 500 hours and 1000 hours was at least 99.999% by weight, and each of intermediate boiling point by-products and high boiling point by-products was undetectable, the content thereof being not more than 1 ppm. Moreover, the halogen content of the diphenyl carbonate was undetectable, the content thereof being not more than 1 ppb.

Example 3

Using the diphenyl carbonate obtained in Example 1, an aromatic polycarbonate was produced using the process described in example 1 in International Publication No. 99/64492. The obtained aromatic polycarbonate having the number average molecular weight of 10500 was injection molded at 310° C. into a test piece (3.2 mm thickness). This test piece had b* value of 3.2 (this value indicating a yellowness in accordance with a CIELAB method) and no yellow tinge, and was uncolored, which was excellent in transparency. After crushing these test pieces by a crushing machine, injection molding of the crushed pieces at 310° C. was repeated five times, whereupon the b* value of the test piece thus obtained was 3.5, and hence marked discoloration was not observed. Moreover, a heat resistance ageing test (120° C., 500 hours) was carried out on the test piece (b* value=3.2) produced by injection molding the above aromatic polycarbonate, whereupon the b* value was 3.5, and hence marked discoloration was not observed.

For the test piece of an aromatic polycarbonate obtained by the same process using diphenyl carbonate containing 150 ppm of each of intermediate boiling point by-products and high boiling point by-products and having a chlorine content of 0.2 ppm, the b* value was 3.6. As described above, the b* value of the molding piece after repeatedly injection molding at 310° C. five times was 4.2, and the b* value after the heat resistance ageing test (120° C., 500 hours) was 4.0. The test pieces in the above two cases exhibited light yellow.

INDUSTRIAL APPLICABILITY

The present invention can be suitably used as a specific industrially useful process that enables a high-purity diaryl carbonate having low contents of intermediate boiling point and high boiling point impurities as required for producing a high-quality and high-performance polycarbonate to be produced stably for a prolonged period of time using as a starting material a reaction mixture containing an alkyl aryl carbonate obtained through a transesterification reaction between a dialkyl carbonate and an aromatic monohydroxy compound.

We claim:

1. An aromatic polycarbonate that is obtained by transesterification between a high-purity diphenyl carbonate and an aromatic dihydroxy compound;
    wherein the high-purity diphenyl carbonate is unsubstituted or substituted with a lower hydrocarbon, and has a halogen content of not more than 0.1 ppm, a content of an intermediate boiling point material of not more than 100 ppm, and a content of by-products having a higher boiling point than that of said diphenyl carbonate of not more than 100 ppm; and
    wherein the high-purity diphenyl carbonate is prepared by a process that comprises taking as a starting material a reaction mixture containing an alkyl aryl carbonate that has been obtained through a transesterification reaction between a dialkyl carbonate and an aromatic monohydroxy compound, continuously feeding the starting material into a reactive distillation column comprising a continuous multi-stage distillation column in which a homogeneous catalyst is present, carrying out a transesterification reaction and distillation simultaneously in said column, continuously withdrawing a low boiling point reaction mixture containing a produced dialkyl carbonate from an upper portion of the column in a gaseous form, and continuously withdrawing a high boiling point reaction mixture containing a diaryl carbonate from a lower portion of the column in a liquid form, wherein:
    (a) said high boiling point reaction mixture is continuously introduced into a high boiling point material separating column A, and continuously subjected to separation by distillation into a column top component $A_T$ containing the diaryl carbonate and a column bottom component $A_B$ containing the catalyst and a high boiling point material,
    (b) said column top component $A_T$ is continuously introduced into a diaryl carbonate purifying column B having a side cut outlet, and continuously subjected to separation by distillation into a column top component $B_T$, a side cut component $B_S$ and a column bottom component $B_B$, the high-purity diaryl carbonate being continuously withdrawn as the side cut component $B_S$, and
    (c) said column top component $B_T$ is continuously introduced into an intermediate boiling point material separating column C having a side cut outlet, and continuously subjected to separation by distillation into a column top component $C_T$ having said alkyl aryl carbonate as a main component thereof, a side cut component $C_S$ having as a main component thereof said intermediate boiling point material having a boiling point between that of said alkyl aryl carbonate and that of said diaryl carbonate, and a column bottom component $C_B$ having said diaryl carbonate as a main component thereof.

2. The aromatic polycarbonate according to claim 1, wherein said diphenyl carbonate is unsubstituted diphenyl carbonate, and the halogen content is not more than 10 ppb, the content of said intermediate boiling point material is not more than 30 ppm, and the content of each of phenyl salicylate, xanthone, phenyl methoxybenzoate, and 1-phenoxycarbonyl-2-phenoxycarboxy-phenylene, which are by-products having a higher boiling point than that of said diphenyl carbonate, is not more than 30 ppm.

3. The aromatic polycarbonate according to claim 2, wherein the content of said intermediate boiling point material is not more than 10 ppm, and the content of the by-products having a higher boiling point than that of said diphenyl carbonate is not more than 50 ppm.

4. The aromatic polycarbonate according to claim 3, wherein the halogen content is not more than 1 ppb, and the content of the by-products having a higher boiling point than that of said diphenyl carbonate is not more than 10 ppm.

* * * * *